United States Patent [19]

Sundelin et al.

[11] 4,410,354
[45] Oct. 18, 1983

[54] SPIRO ETHER HERBICIDES

[75] Inventors: Kurt G. R. Sundelin, Modesto; James E. Powell, Ripon; Willy D. Kollmeyer, Modesto, all of Calif.

[73] Assignee: Shell Oil Company, Houston, Tex.

[21] Appl. No.: 344,282

[22] Filed: Feb. 1, 1982

[51] Int. Cl.³ .................. A01N 43/40; C07D 491/10; C07D 491/20; C07D 495/20
[52] U.S. Cl. ........................................ 71/94; 549/331; 549/334; 549/343; 424/283; 424/263; 546/19; 71/88
[58] Field of Search ...................... 549/331, 334, 343; 424/283, 263; 546/19; 71/88, 94

[56] References Cited

U.S. PATENT DOCUMENTS 4,014,905 3/1977 Skorianetz et al. ................. 549/331

Primary Examiner—Henry R. Jiles
Assistant Examiner—Robert C. Whittenbaugh

[57] ABSTRACT

Certain spiro ether derivatives are useful as herbicides.

14 Claims, No Drawings

SPIRO ETHER HERBICIDES

BACKGROUND OF THE INVENTION

Field of the Invention

The present invention relates to novel spiro ether derivatives, their use for controlling undesirable plant growth and compositions containing these novel derivatives.

SUMMARY OF THE INVENTION

The present invention relates to novel spiro ether derivatives of Formula I

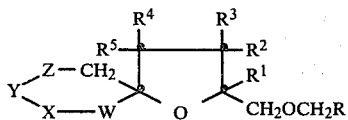

wherein $R^1$, $R^2$, $R^3$, $R^4$, $R^5$ each individually is a hydrogen atom or an alkyl group containing from 1 to 4 carbon atoms, W is an oxygen atom or —$CH_2$—; X is an oxygen atom or —$CH_2$—; Y is a carbon-carbon bond, an oxygen atom, —$CH_2$—, —$C_2H_4$— or —$CHR^6$— in which $R^6$ is an alkoxymethyl group containing from 1 to 4 carbon atoms in the alkyl portion thereof; Z is a carbon-carbon bond, an oxygen atom, —$CH_2$— or —$C_2H_4$—; with the proviso that no two adjacent of W, X, Y and Z are simultaneously either oxygen atoms or —$C_2H_4$— and the sum of the ring atoms in W, X, Y and Z is an integer of from 2 to 5; and R is an alkenyl or alkynyl group containing from 2 to 4 carbon atoms, a 2-furanyl group, a 2-pyridinyl group or a phenyl group optionally substituted by one or more of halogens selected from chlorine, bromine, fluorine, amino, monoalkylamino, dialkylamino, alkyl, haloalkyl, alkoxy, haloalkoxy, or alkylthio containing from 1 to 3 carbon atoms in each alkyl group.

Preferably, $R^1$ is a hydrogen atom or a methyl or ethyl group, especially an ethyl group and $R^2$, $R^3$, $R^4$ and $R^5$ each is a hydrogen atom.

Preferably, W is an oxygen atom or —$CH_2$—, X is an oxygen atom or —$CH_2$—; Y is an oxygen atom, —$CH_2$—, —$C_2H_4$— or —$CHR^6$— in which $R^6$ is methoxymethyl; Z is an oxygen atom or —$CH_2$—; and the sum of the ring atoms in W, X, Y and Z is an integer of from 3 to 5. One preferred subclass of the invention is when W and Z each is —$CH_2$—; and one of X and Y is —$CH_2$— and the other is an oxygen atom. Another preferred subclass of the invention is when W is —$CH_2$—; X and Z each is an oxygen atom and Y is —$C_2H_4$—.

Preferably, R is an ethynyl group, a 2-pyridinyl group or an optionally substituted phenyl group, for example, a 4-fluorophenyl, a 2-chlorophenyl, a 2-fluorophenyl, a 2-methylphenyl, a 2,6-dichlorophenyl, a 2,5-dichloro-3-aminophenyl, a 2-(trifluoromethyl)phenyl, a 2-(difluoromethoxy)phenyl, a phenyl group or the like.

A preferred subclass of the invention is when R is an ethynyl group, 2-pyridinyl group or a phenyl group substituted by one or two of a chlorine atom, a fluorine atom or a methyl group, preferably in the 2-, 4- or 2,6-positions. One further preferred subclass of the invention is when R is 2-methylphenyl, a second preferred subclass is when R is 2-chlorophenyl and a third preferred subclass is when R is 2-fluorophenyl.

Compounds possessing substantially the same utility as those described above and which can be prepared in like manner are equivalents thereof and include compounds wherein, for example, R is an unsaturated, pseudo-aromatic, aromatic or heteroaromatic moiety, including but not limited to cyano, cyclopropyl, naphthyl, imidazolyl, triazolyl, thiadiazolyl, pyrazinyl, pyridazinyl, triazinyl, pyrrolyl, cyclohexenyl, N-methylimidazolyl, N-methylpyrazolyl, (is)oxazolyl, pyrimidinyl, (iso)thiazolyl, thienyl, and the like.

Non-limiting examples of species of the invention include:

2-ethyl-2-(benzyloxymethyl)-1,7-dioxaspiro[4.5]decane,
2-ethyl-2-(benzyloxymethyl)-1,8-dioxaspiro[4.5]decane,
2-ethyl-2-(benzyloxymethyl)-1,6-dioxaspiro[4.4]nonane,
2-ethyl-2-(benzyloxymethyl)-1,6-dioxaspiro[4.5]decane,
2-ethyl-2-(benzyloxymethyl)-1,7-dioxaspiro[4.4]nonane,
6-ethyl-6-(benzyloxymethyl)-2,5-dioxaspiro[3.4]octane,
2-ethyl-2-(benzyloxymethyl)-1,7,9-trioxaspiro[4.5]decane,
2-ethyl-2-(benzyloxymethyl)-1,6-dioxaspiro[4.6]undecane,
2-ethyl-2-(benzyloxymethyl)-1,7-dioxaspiro[4.6]undecane,
2-ethyl-2-(benzyloxymethyl)-1,8-dioxaspiro[4.6]undecane,
2-ethyl-2-(benzyloxymethyl)-1,6,9-trioxaspiro[4.5]decane,
2-ethyl-2-(benzyloxymethyl)-1,6,8-trioxaspiro[4.5]decane,
2-ethyl-2-(benzyloxymethyl-1,6,8-trioxaspiro[4.4]nonane,
2-ethyl-2-(benzyloxymethyl)-1,6,8-trioxaspiro[4.6]undecane,
2-ethyl-2-(benzyloxymethyl)-1,6,9-trioxaspiro[4.6]undecane,
2-ethyl-2-(benzyloxymethyl)-1,6,10-trioxaspiro[4.6]undecane,
2-ethyl-2-(benzyloxymethyl)-1,7,9-trioxaspiro[4.6]undecane,
2-ethyl-2-(benzyloxymethyl)-1,7,10-trioxaspiro[4.6]undecane, and the corresponding 2-((2-fluorobenzyl)oxymethyl), 2-((2-methylbenzyl)oxymethyl), 2-((2-chlorobenzyl)oxymethyl), and (2-pyridinylmethoxy)methyl derivatives.

The compounds of Formula I exhibit geometrical and optical isomerism and may be prepared in geometrical and/or optically active forms, which may be mixed, or as racemates, which may be resolved into optically active and/or geometrical forms. The various individual optical and geometrical forms and various combinations thereof of the materials of the invention usually have some differences in herbicidal properties. The present invention contemplates all the herbicidally active forms resulting from synthesis, and deliberately created mixtures.

The Compounds of the Invention described by Formula 1 are prepared by treating the appropriately substituted oxaspiroalkane-2-methanol with a compound of the formula $RCH_2X$ in which X is a halogen atom, such as bromine, chlorine or iodine or is a mesylate, tosylate radical or the like, preferably in the presence of a strong base and an inert diluent, and preferably in the presence of a catalyst. The strong base is suitably an alkali metal hydride, amide, hydroxide or carbonate, including, for example, sodium hydride, sodium amide, sodium hydroxide, potassium carbonate and the like. Inert diluents are suitably organic solvents, such as ethers, aromatic hydrocarbons, chlorinated hydrocarbons and the like, including, for example, diethyl ether, tetrahydrofuran, 1,2-dimethoxyethane, toluene, methylene chloride and the like. Suitable catalysts are organic bases, such as tertiary amines and ammonium compounds, for example, triethylamine, benzyltriethylammonium chloride and the like. The reaction is usually carried out under normal pressures and ambient temperatures. Suitable temperatures for the reaction are from about 0° to about 120° C., preferably from about 20° to about 100° C. The product ethers are recovered and isolated by conventional techniques.

The oxaspiroalkane-2-methanols of the Formula II

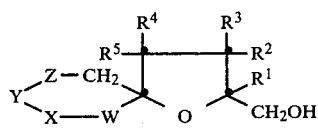

wherein $R^1$, $R^2$, $R^3$, $R^4$, $R^5$, W, X, Y and Z, are as previously defined as in the Formula I are prepared by one or more of the following processes.

(a) From a mono-unsaturated heterocyclic (di)oxygen compound, such as dihydropyran, corresponding to the ring containing the W, X, Y, Z in Formula II, by hydroboration/oxidation to a beta-hydroxy ether, e.g., with borane and hydrogen peroxide, followed by oxidation, e.g. with dimethyl sulfoxide and oxalyl chloride, to the corresponding ketone, alkylation with an unsaturated Grignard reagent to a tertiary alcohol and epoxidation-cyclization, e.g. in the presence of peracetic acid in acetic acid containing anhydrous sodium acetate, to yield the desired di- (or tri-) oxaspiroalkane-2-methanol of Formula II;

(b) From a 2-hydroxymethyl (di)-oxacycloalkane, for example, tetrahydrofurfuryl alcohol, by treatment with thionyl chloride or phosphorus tribromide to yield the corresponding chloride or bromide followed by dehydrohalogenation in the presence of base to an alpha-methylene cyclic ether, which is cyclo-added to (meth)- or (eth)-acrolein, under non-acidic conditions, to give a spiro ketal, which upon oxidation, e.g. with m-chloroperbenzoic acid, affords the corresponding ring contracted aldehyde and reduction of this aldehyde, e.g. with Raney nickel and triethylamine, to yield the desired di- (or tri-) oxaspiroalkane-2-methanol of Formula II; and (c) From condensation of a lithium substituted mono unsaturated heterocyclic (di)oxygen compound corresponding to the ring containing W, X, Y and Z, e.g. lithium dihydropyran, with a halo-epoxyalkane, e.g., 1,2-epoxy-2-ethyl(-4-iodo)butane, to yield the corresponding epoxyalkylated heterocycle, e.g. 6-(3-ethyl-(3,4-epoxybutyl)-3,4-dihydro-2H-pyran, and acid cleavage of the epoxide, e.g. with hydrochloric acid, to yield the desired di- (or tri-) oxaspiroalkane-2-methanol of Formula II.

The Compounds of the Invention have been found useful for influencing plant growth and controlling the growth of unwanted plants, being particularly active with respect to grassy weeds and some broadleaf plants. For example, the compounds can change plant morphology, depress the growth of plants, inhibit germination; or totally or selectively kill plants depending on the amounts used. As herbicides, they appear to be more effective when applied preemergence (applied to the soil before the seeds have sprouted) than when applied postemergence (applied to the foliage).

For application to the locus to be treated, e.g. herbicidal application, the compounds of the invention preferably are formulated with a carrier, or a surface-active material, or both.

By "carrier" is meant a solid or a fluid material, which may be inorganic or organic and of synthetic or natural origin, with which the compound of the invention is mixed or formulated to facilitate its application to the plant, seed, soil or other object to be treated, or its storage, transport or handling.

Suitable solid carriers are natural and synthetic clays and silicates, for example, natural silicas such as diatomaceous earths; magnesium silicates, for example, talcs, magnesium aluminum silicates, for example, attapulgites and vermiculites; aluminum silicates, for example, kaloinites, montmorillonites and micas; calcium carbonates; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; solid polychlorophenols; bitumen, waxes such as, for example, beeswax, paraffin wax, and chlorinated mineral waxes; and solid fertilizers, for example, superphosphates.

Examples of suitable fluid carriers are water, alcohols, such as, for example, isopropanol, glycols; ketones such as, for example, acetone, methyl ethyl ketone, methyl isobutyl ketone and cyclohexanone; ethers; aromatic hydrocarbons such as, for example, benzene, toluene and xylene; petroleum fractions such as, for example, kerosene, light mineral oils; chlorinated hydrocarbons such as, for example, carbon tetrachloride, perchloroethylene, trichloroethane, including liquefied normally vaporous gaseous compounds. Mixtures of different liquids are often suitable. The surface-active agent may be an emulsifying agent or a wetting agent; it may be nonionic or ionic. Any of the surface-active agents usually applied in formulating herbicides or insecticides may be used. Examples of suitable surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols and alkylphenols, for example, p-octylphenol or p-octylcresol, with ethylene oxide and/or propylene oxide; sulfates or sulfonates of these condensation products, alkali or alkaline earth metal salts, preferably sodium salts, or sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions may be formulated as wettable powders, dusts, granules, solutions, emulsifiable concentrates, emulsions, suspension concentrates and aerosols. Wettable powders are usually compounded to contain 25, 50 and 75% by weight of toxicant and usually contain in addition to solid carrier, 3-10% by weight of a dispersing agent, 15% of a surface-active agent and where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of toxicant. Granules are usually prepared to have a size between 10 to 100 BS mesh (1.676-0.152 mm), and may be manufactured by agglomeration or impregnation techniques. Generally, granules will contain 0.5-25% by weight toxicant and 0-1% by weight of additives such as stabilizers, slow-release modifiers and binding agents. Emulsifiable concentrates usually contain, in addition to the solvent and, when necessary, cosolvent, 10-50% weight per volume toxicant, 2-20% weight per volume emulsifiers and 0-20% weight per volume of appropriate additives such as stabilizers, penetrants and corrosion inhibitors.

Suspension concentrates are compounded so as to obtain a stable, nonsedimenting, flowable product and usually contain 10-75% weight toxicant, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as antifreeze agents for water.

Aqueous dispersions and emulsions, for example, compositions obtained by diluting a wettable powder or a concentrate with water, also are suitable. The said emulsions may be of the water-in-oil or of the oil-in-water type, and may have a thick mayonnaise-like consistency.

The compositions may also contain other ingredients, for example, other compounds possessing pesticidal, especially insecticidal, acaricidal, herbicidal or fungicidal properties.

ILLUSTRATIVE EMBODIMENTS

The invention is illustrated by the following embodiments which describe the preparation of typical species of the invention. The embodiments are presented for the purpose of illustration only, and should not be regarded as limiting the invention in any way. The identity of the products, including intermediates, was confirmed by elemental, infrared and nuclear magnetic resonance spectral (NMR) analyses as necessary.

Embodiment I—Tetrahydropyran-3-ol 50.4 g of freshly distilled dihydropyran was dissolved in 170 ml of tetrahydrofuran. To this stirred solution under nitrogen, was added dropwise 300 ml of 1 M borane in tetrahydrofuran at $-5°$ to $+5°$ C. After 1 hour and 40 minutes, 120 ml of 10% sodium hydroxide was added dropwise at $0°-3°$ C. The reaction mixture was warmed to $32°$ C. and 68 ml of 30% hydrogen peroxide was added dropwise. The reaction mixture was warmed to about $50°$ C. and after 1½ hours, cooled to $30°$ C. After addition of 190 g of potassium carbonate, the resulting layers were separated. The aqueous layer was extracted twice with 100 ml of ether. The combined organic layers were dried with $MgSO_4$ and stripped to yield 59 g of a pale green liquid. This liquid was fractionated by distillation to yield the desired product, b.p. $57°-97°$ (2.5-0.7 mm).

Embodiment II—Tetrahydropyran-3-one 91.27 g of pyridinium chlorochromate was dissolved in 275 ml of methylene chloride. To this stirred solution under nitrogen, was added in one portion 28.80 g of tetrahydropyran-3-ol in 30 ml of methylene chloride. The resulting mixture turned black. After 5 hours, the reaction mixture was diluted with twice its volume of ether and decanted. The remaining black tarry material was rinsed three times with ether. The combined ether solutions were passed through a column of florisil and stripped. The resulting emerald green liquid was dissolved in anhydrous ether, again passed through florisil, and stripped to yield 20.08 g of a pale green liquid. Vacuum distillation afforded the desired product as a liquid, b.p. $66°-69°$ (20 mm).

Embodiment III—Tetrahydro-3-(3-methylenepentyl)-2H-pyran-3-ol

A mixture of 5.60 g of magnesium shaving and a crystal of iodine in dry tetrahydrofuran was allowed to stand under nitrogen for 20 minutes. Then 0.25 ml of methyl iodide and 5 ml of a solution of 20.85 g of 1,1,1-tris(chloromethyl)propane in 25 ml of tetrahydrofuran was added dropwise with stirring. When the reaction was initiated by warming, the remainder of the 1,1,1-tris(chloromethyl)propane solution was added dropwise. The resulting light gray mixture was heated to reflux for an additional 30 minutes. After cooling with a dry ice/isopropanol bath, a solution of 10.0 g of tetrahydropyran-3-one in 10 ml tetrahydrofuran was added dropwise at $-50°$ to $-40°$ C. The reaction mixture was then stirred 1 hour at $-70°$ C. and 30 minutes at $-70°$ to $-25°$ C. The chilled mixture was poured into 300 ml of chilled mixture of 300 ml diethyl ether and 200 ml saturated ammonium chloride cooled with an ice water bath. The resulting phases were separated and the aqueous phase was extracted twice with 200 ml ether. The combined ether extracts were washed with saturated sodium chloride, dried with $Na_2SO_4$ and vacuum concentrated to yield 15.0 g of pale yellow liquid. By silica gel chromatography, using the dry column technique and 20:4:1 hexane-ethyl acetate-tetrahydrofuran eluent, two fractions were obtained, the first of which was 4.5 g of the desired product as a colorless liquid and the second of which was 2.0 g of the desired product plus some starting tetrahydropyran-3-one.

Embodiment IV—2-Ethyl-1,7-dioxaspiro[4.5]decane-2-methanol

To a solution of 5.75 g of tetrahydro-3-(3-methylenepentyl)-2H-pyran-3-ol in 40 ml methylene chloride was added in four portions, 6.5 g of 40% peracetic acid in acetic acid containing 145 mg of anhydrous sodium acetate. A temperature increase from $20°$ C. to $37°$ C. resulted. The resulting solution was refluxed for 1 hour and stirred at ambient temperature for 4 hours. The resulting mixture was diluted with 60 ml of methylene chloride and washed with 100 ml of water. The organic phase was washed successively with two 100 ml portions of 25% potassium carbonate, and 100 ml of saturated sodium chloride, dried with $MgSO_4$ and vacuum concentrated to leave 5.7 g of the desired product as an oil.

Embodiment V—2-Ethyl-2-((phenylmethoxy)methyl)-1,7-dioxaspiro[4.5]decane 6.5 g of a 57% dispersion of sodium hydride in mineral oil was washed with hexane under nitrogen and suspended in 15 ml of dimethylformamide. A solution of 2.6 g of 2-ethyl-1,7-dioxaspiro[4.5]decane-2-methanol in 5 ml of dimethylformamide was added to the dispersion and the resulting mixture was stirred for 45 minutes with water bath cooling. A solution of 1.8 g of benzyl chloride in 3 ml of dimethylformamide was added in one portion. After the reaction mixture was stirred for 22 hours, the dimethylformamide was evaporated and the residue was diluted with 200 ml of ether. The ether solution was washed successively with two 50 ml portions of water and 30 ml of saturated sodium chloride, dried with MgSO$_4$, and vacuum concentrated to leave 3.4 g of a pale yellow oil, which was distilled to give the desired product based on IR and NMR analyses, b.p. 127° C. (0.03 mm).

Embodiment VI—2-Ethyl-2-((2-pyridinylmethoxy)methyl)-1,7-dioxaspiro[4.5]decane Following procedures similar to Embodiments I-V above, 2-ethyl-1,7-dioxaspiro[4.5]decane-2-methanol was treated with 2-picolinyl chloride in the presence of sodium hydride to yield the desired product as a pale amber oil, b.p. 123° C. (0.006 mm).

Embodiment VII—2-Ethyl-2-((2-fluorophenylmethoxy)methyl)-1,7-dioxaspiro[4.5]decane Following procedures similar to Embodiments I-V, 2.00 g of 2-ethyl-1,7-dioxaspiro[4.5]decane-2-methanol was treated with 1.54 g of 2-methylbenzyl chloride in the presence of sodium hydride to yield the desired product as a pale yellow oil.

Embodiment IX—2-Ethyl-2-((2-fluorophenylmethoxy)methyl)-8-(methoxymethyl)-1,7-dioxaspiro[4.5]decane Following procedures similar to Embodiments I-V, 1.67 g of 2-ethyl-8-(methoxymethyl)-1,7-dioxaspiro[4.5]decane-2-methanol was treated with 1.09 g of 2-fluorobenzyl chloride in the presence of sodium hydride to yield the desired product as a colorless oil.

Embodiment X—3,5-Dioxaoctan-1,8-dioic Acid

To a 100 ml solution of 70% nitric acid was added 24 ml of triethylene glycol at 65° C. In a short time, gas was generated and the solution became a very pale yellow. Additional triethylene glycol to total 20 g was added dropwise to maintain a temperature of about 48° C. The resulting reaction mixture warmed to 98° C. and became brown. After being cooled to 20° C. for 20 minutes with an ice bath, the reaction mixture was warmed to 45° C. for 40 minutes, then to 80° C. for 20 minutes and then allowed to cool to ambient temperature. The resulting product was partially stripped and 120 ml of toluene was added to azeotrope out the water. The resulting two phases of liquid were stripped to yield 40.40 g of brown liquids and solids. The liquids were decanted off leaving 28.95 g of the desired product.

Embodiment XI—Diethyl 3,6-Dioxaoctanedioate

Through a solution of 28.95 g of 3,6-dioxaoctan-1,8-dioic acid in 250 ml of absolute ethanol was bubbled hydrogen chloride gas. After three hours, the reaction mixture was stripped and the residue was dissolved in ethyl acetate. The resulting solution was washed twice with saturated sodium bicarbonate solution, water, sodium chloride solution, dried and stripped to yield 26.60 g of brown liquid, which was vacuum distilled to yield the desired product, b.p. 104° (0.125 mm).

Embodiment XII—5-(Ethoxycarbonyl)-1,4-dioxapin-6-one 7.25 g of a 50% dispersion of sodium hydride in oil was washed with pentane and suspended in 192 ml of toluene, and 7.7 ml of tert-butanol was added. The reaction mixture was refluxed under nitrogen and 12.62 g of diethyl 3,6-dioxaoctanedioate in 192 ml of toluene was added dropwise. After about 40 hours, the addition was complete. The reaction mixture was refluxed for 3 hours, cooled, and 15.4 ml of acetic acid was added dropwise to adjust the pH of the reaction mixture to 5. The mixture was washed twice with saturated sodium chloride solution, dried and stripped to yield 5.40 g of brownish liquid. The combined aqueous washes were extracted three times with ethyl acetate, and the combined extracts were dried and stripped to yield 1.10 g of brown liquid. Distillation of the latter gave 0.15 g of a yellow liquid which had the same IR as the earlier 5.40 g of brown liquid. These two fractions combined gave 5.55 g of the desired product.

Embodiment XII—1,4-Dioxepin-6-one

The entire product of Embodiment XII above was suspended in 150 ml of 10% hydrochloric acid and refluxed for 3 hours and 20 minutes under nitrogen. After removal of heat, the reaction mixture was saturated with potassium carbonate. After the evolution of heat and gas, the mixture was extracted three times with ethyl acetate. The combined ethyl acetate extracts were dried and stripped to yield 1.80 g of the desired product as a brown liquid.

Embodiment XIV—Tetrahydro-6-(3-methylenepentyl)-1,4-dioxepin-6-ol

To 0.99 g of dry magnesium shavings was added 14 ml of dry tetrahydrofuran and a small crystal of iodine. After 20 minutes, 0.25 ml of 1,2-dibromoethane was added by syringe and then 0.5 ml of a 70% tetrahydrofuran solution of 1,1,1-tris(chloromethyl)propane. The reaction mixture was warmed to reflux and more 70% 1,1,1-tris(chloromethyl)propane solution was added to total 5.29 g at a rate to maintain reflux. After the addition was complete, the reaction was refluxed for an additional half hour. After the addition of 10 ml of tetrahydrofuran, the reaction mixture was cooled to −60° C. and 2.06 g of 1,4-dioxepin-6-one in 10 ml of tetrahydrofuran was added dropwise. After 2.5 hours at −60° C., the reaction mixture was warmed to −20° C. and poured into a mixture of 200 ml of saturated ammonium chloride and diethyl ether. The resulting layers were separated and the aqueous layer was extracted twice with diethyl ether. The combined organic layers were washed with water, dried and stripped to yield 3.05 g of the desired product as a dark yellow liquid.

Embodiment XV—2-Ethyl-1,7,10-trioxaspiro[4.6]undecane-2-methanol

To a stirred solution of 3.22 g of 3-chloroperbenzoic acid dissolved in 20 ml of methylene chloride under nitrogen, was added dropwise 3.05 g of tetrahydro-6-(3-methylenepentyl)-1,4-dioxepin-6-ol while maintaining the temperature below 30° C. using a water bath. After six hours and 20 minutes, the reaction mixture was washed with a 25% solution of potassium carbonate and a saturated sodium chloride solution, dried and stripped to yield 2.10 g of the desired product as a dark brown liquid.

Embodiment XVI—2-Ethyl-2-((2-fluorophenyl)methoxymethyl)-1,7,10-trioxaspiro[4.6]undecane 0.58 g of a 50% sodium hydride solution in mineral oil was washed with pentane and suspended in 5 ml of dimethylformamide. To this stirred suspension under nitrogen at 0° C. was added dropwise 2.10 g of 2-ethyl-1,7,10-trioxaspiro[4.6]undecane-2-methanol in 6 ml of dimethylformamide. After 1.5 hours, 1.55 g of o-fluorobenzyl chloride in 2 ml of dimethylformamide was added dropwise. The reaction mixture was allowed to warm to room temperature. After three hours, the reaction mixture was diluted with three times its volume of water, and extracted three times with ethyl acetate. The combined ethyl acetate extracts were washed with saturated sodium chloride solution, dried and stripped to yield 3.43 g of brown liquid. Distillation with a kugelrohr apparatus yielded a fraction, b.p. 120°–130° C. (0.02 mm), which was chromatographed on a silica gel plate to yield 1.10 g of the desired product as a pale yellow liquid.

Embodiment XVII—Tetrahydro-4-(3-methylenepentyl)-2H-pyran-4-ol

To 8.50 g of dry magnesium shavings was added 100 ml of tetrahydrofuran and a small crystal of iodine. After 20 minutes, 0.5 ml of 1,2-dibromoethene was added using a syringe followed by the dropwise addition of 5 ml of a 70% solution of 1,1,1-tris(chloromethyl)propane in tetrahydrofuran with evolution of heat and gas. While stirring, additional 1,1,1-tris(chloromethyl)propane solution was added, to total 44.7 g at a rate to maintain reflux. The refluxing was continued for an additional 0.5 hour. Then, the reaction mixture was cooled to −62° to −43° C. and 15.0 g of 4H-pyran-4-one (Aldrich) in 20 ml of tetrahydrofuran was added dropwise. After 1 hour at −60° C., the reaction mixture was allowed to warm to −20° C. and then poured into a mixture of ice-cold diethyl ether (500 ml) and saturated ammonium chloride (350 ml). The aqueous fraction was extracted twice with 300 ml diethyl ether. The combined ether solutions were washed with saturated sodium chloride solution, dried and stripped to yield 16.52 g of the desired product as a pale yellow liquid.

Embodiment XVIII—2-Ethyl-1,8-dioxaspiro[4.5]decane-2-methanol

To a stirred solution of 16.52 g of tetrahydro-4-(3-methylenepentyl)-2H-pyran-4-ol in 100 ml of methylene chloride under nitrogen was added portionwise 15.32 g of peracetic acid (with 0.40 g of anhydrous sodium acetate added). The reaction mixture was refluxed for 1 hour, allowed to set for 4 hours, diluted with 150 ml of methylene chloride, washed successively with water, twice with 25% potassium carbonate, and saturated sodium chloride, dried and filtered. The resulting solution was stripped to yield 12.42 g of the desired product as a pale yellow liquid.

Embodiment XIX—2-Ethyl-2-((2-fluorophenyl)methoxymethyl)-1,8-dioxaspiro[4.5]decane 0.75 g of a 50% sodium hydride solution in mineral oil was washed with pentane and suspended in 8 ml of dimethylformamide. To this stirred solution under nitrogen at 3°–7° C. was added dropwise 2.50 g of 2-ethyl-1,8-dioxaspiro[4.5]decane-2-methanol in 20 ml of dimethylformamide. The reaction mixture was allowed to warm to room temperature. After 2 hours the temperature was reduced to 4°–6° C. and 1.99 g of O-fluorobenzyl chloride in 2 ml of dimethylformamide was added dropwise. The reaction mixture was allowed to rise to room temperature, and after four hours and 20 minutes, diluted to three times its volume of water and extracted three times with ethyl acetate. The combined ethyl acetate extracts were washed successively with water and saturated sodium chloride solution, dried and stripped to yield 3.30 g dark yellow liquid. The liquid was chromatographed on a silica gel column using ethyl acetatehexane as eluent to yield three fractions. The last two of these fractions were combined and distilled with a kugelrohr apparatus. A pale yellow liquid, 0.65 g, was collected, b.p. 130° (1 mm), and chromatographed on a silica gel plate to yield 0.68 g of the desired product.

Embodiment XX—2-Ethyl-2-(phenylmethoxymethyl)-1,8-dioxaspiro[4.5]-decane

Following procedures similar to those of Embodiments XVII–XIX, 2.50 g of 2-ethyl-1,8-dioxaspiro[4.5]-decane-2-methanol was treated with 2.35 g of benzyl bromide in the presence of sodium hydride to yield 0.90 g of the desired product as a clear liquid, b.p. 130° C. (0.15 mm).

Embodiment XXI—2-Ethyl-2-((2-pyridinyl)methoxymethyl)-1,8-dioxaspiro[4.5]decane Following procedures similar to Embodiments XVII–XIX, 1.10 g of 2-ethyl-1,8-dioxaspiro[4.5]decane-2-methanol was treated with 1.35 g of 2-picolinyl chloride hydrochloride in the presence of sodium hydride to yield 1.00 g of the desired product as pale yellow liquid.

Embodiment XXII—4-Bromo-2-ethyl-1-butene

To a stirred solution of 53.4 g of dry magnesium shavings in 300 ml of dry tetrahydrofuran under nitrogen was added 271 g of a 70% solution of 1,1,1-tris(chloromethyl)propane in 200 ml of dry tetrahydrofuran. After 24 hours, the reaction mixture was filtered and 90 g of bromine was added dropwise over 2 hours while maintaining the reaction mixture at −15° to −20° C. The reaction mixture was filtered, and the solids washed into a hydrogen chloride-saturated sodium chloride mixture. The resulting organic layer was washed with saturated sodium bicarbonate and sodium bisulfite, dried and stripped to yield 73 g of a light brown oil. Fractional distillation of this oil gave 27.3 g of the desired product, b.p. 60°–70° C. (30–40 mm).

Embodiment XXIII—4-Bromo-1,2-epoxy-2-ethylbutene

To a vigorously stirred mixture of 27.3 g of 4-bromo-2-ethyl-1-butene in 1400 ml methylene chloride and 450 ml of 0.5 M sodium bicarbonate, this was added portionwise over 2 hours 29 g of 85% m-chloroperbenzoic acid. After three days, the methylene chloride layer was separated and washed successively with a dilute potassium carbonate and sodium bisulfite mixture and then water, dried, and fractionally distilled to give 11.6 g of the desired product, b.p. 83°-89° C. (15-20 mm).

Embodiment XXIV—1,2-Epoxy-2-(ethyl)-4-iodobutane

To a stirred solution of 12 g of freshly powdered sodium iodide in 100 ml of methyl ethyl ketone was added 14 g of 4-bromo-1,2-epoxy-2-(ethyl)butane. After 24 hours, 2 g of sodium iodide was added and the mixture was stirred for 24 hours more. The reaction mixture was filtered, the solvent was removed from the filtrate, diethyl ether was added to the residue, and the resulting mixture was washed with a dilute potassium carbonate and sodium bisulfite mixture. The ether layer was dried and the solvent was distilled to give 19.8 g of a clear, colorless oil which was fractionally distilled to give 11.3 g of the desired material, b.p. 89°-99° C. (8-16 mm).

Embodiment XXV—6-(3-Ethyl-(3,4-epoxybutyl))-3,4-dihydro-2H-pyran

To a stirred solution of 3.2 g of dihydropyran and 1.4 g of dry tetrahydrofuran at 0° C. was added dropwise 50 ml 2 M tert-butyl lithium. The reaction was allowed to warm to room temperature, then cooled to −10° to −20° C., and 10 g of 1,2-epoxy-2-(ethyl)-4-iodobutane and 0.7 g of hexamethylphosphoramide was added dropwise over 10 minutes. After stirring for 2 hours at −15° to −20° C., 6-8 ml of dry tetrahydrofuran was added. The reaction mixture was allowed to warm to room temperature, stirred for a total of 2 hours, 40-50 ml of hexane was added, and the mixture was washed with water and then with a saturated sodium chloride and sodium bisulfite mixture, dried and vacuum stripped to give 6 g of the desired material as an oil.

Embodiment XXVI—2-Ethyl-1,6-dioxaspiro[4.5]decane-2-methanol

To 5.5 g of 6-(3-ethyl-(3,4-epoxybutyl))-3,4-dihydro-2H-pyran was added a solution of 2 ml of 10% hydrochloric acid in 25 ml of tetrahydrofuran. The reaction mixture was stirred under nitrogen for five days and then poured into 150 ml of diethyl ether. The resulting solution was washed twice with 50 ml of saturated sodium bicarbonate solution, and dried, and the solvent was removed under high vacuum to yield 6 g of the desired product as a dark brown oil.

Embodiment XXVII—2-Ethyl-2-((2-(fluorophenyl)methoxy)methyl)-1,6-dioxaspiro[4.5]decane Following procedures similar to Embodiments V and XVI, 2-ethyl-1,6-dioxaspiro[4.5]decane-2-methanol was treated with 2-fluorobenzyl chloride in the presence of sodium hydride to yield the desired ether.

Embodiment XXVIII—2-(Chloromethyl)tetrahydrofuran

A solution of 133 g of tetrahydrofurfuryl alcohol in 160 ml of benzene was treated with 170 g of thionyl chloride in the presence of 0.7 ml of pyridine as catalyst to yield 80.3 g of the desired product, b.p. 73°-74° C. (43 torr.).

Embodiment XXIX—2-Methylenetetrahydrofuran

In a glass flask was pretreated with concentrated aqueous ammonia and dried by distilling benzene from it, 40.0 g of 2-(chloromethyl)tetrahydrofuran was treated with 37.2 g of potassium hydroxide in 80 ml of diethylene glycol to yield 12.5 g of the desired product, b.p. 98°-101° C.

Embodiment XXX—8-Methyl-1,6-dioxaspiro[4.5]dec-7-ene

A stirred mixture of 20.0 g of 2-methylenetetrahydrofuran, 17.7 g of reagent grade methacrolein and 0.4 g of potassium carbonate was maintained at 75° C. under nigrogen atmosphere for 7 days. Distillation of the reaction mixture yielded 19.1 g of the desired product, b.p. 65°-66° C. (4 torr.).

Embodiment XXXI—2-Methyl-1,6-dioxaspiro[4.4]nonane-2-carboxaldehyde

To a cooled and stirred solution of 8.80 g of 85% m-chloroperbenzoic acid in 120 ml of methylene chloride was added 6.16 g of 8-methyl-1,6-dioxaspiro[4.5]dec-7-ene in 20 ml of methylene chloride. The exothermic reaction was kept below 15° C. After 15 minutes, the mixture was poured into 600 ml of saturated potassium carbonate. The resulting organic layer was then washed with aqueous base, dried and distilled to yield 4.37 g of the desired product as a colorless liquid, b.p. 65°-70° C. (1 torr.).

Embodiment XXXII—2-Methyl-1,6-dioxaspiro[4.4]nonane-2-methanol

A solution of 1.70 g of 2-methyl-1,6-dioxaspiro[4.4]nonane-2-carboxaldehyde in tetrahydrofuran was hydrogenated at 60 p.s.i. and 20° C. for 5 hours in the presence of 1.0 g triethylamine promoter and Raney nickel, that had been rinsed in tetrahydrofuran. When all of the starting material had disappeared, the mixture was treated with magnesium sulfate and filtered. Distillation of the filtrate gave 1.43 g of the desired product as a colorless liquid, b.p. 65°-70° C. (1 torr.).

Embodiment XXXIII—2-Methyl-2-((phenylmethoxy)methyl)-1,6-dioxaspiro[4.4]nonane A solution of 1.70 g of 2-methyl-1,6-dioxaspiro[4.4]nonane-2-methanol in 20 ml of dimethylformamide was treated sequentially with 0.60 g of 60% sodium hydride-mineral oil dispersion at 15°-25° C. for 1 hour and then with 1.71 g of benzyl bromide at 0°-25° C. for 1 hour. The resulting mixture was poured into 150 ml of water and extracted with diethyl ether. The ether extract was washed with water, dried and distilled to yield 1.40 g of the desired product as a colorless liquid, b.p. 105°-110° C. (0.3 torr.).

Protection of a locus or area from undesirable plants is effected by applying a Compound of Formula I of the Invention, ordinarily in a composition of one of the aforementioned types, to the foliage of the plants or plant growth medium, e.g., soil in which the plant is growing or in which the seeds are present or will be planted. The Compounds of the Invention, of course, are applied in amounts sufficient to exert the desired action.

The amount of the Compounds of the Invention to be used in controlling undesirable vegetation will naturally depend on the condition of the vegetation, the degree of activity desired, the formulation used, the mode of application, the climate, the season of the year, and other variables. Recommendations as to precise amounts are, therefore, not possible. In general, however, application to the locus to be protected of from 0.05 to 10.0 kilograms per hectare of the area will be satisfactory for practical applications.

EXAMPLES OF HERBICIDAL ACTIVITY

In the following examples, the species of plants that were tested were:

Barnyardgrass (watergrass)—*Enchinochloa crus-galli*
Large crabgrass—*Digitaria sanguinalis*
Downy brome—*Bromus tectorum*
Yellow foxtail—*Setaria lutescens*
Redroot pigweed—*Amaranthus retroflexus*
Sicklepod—*Cassia obtusifolia*
Velvetleaf—*Abutilon theophrasti*
Garden cress—*Lepidium sativum*
Johnsongrass—*Sorghum halepense*

Embodiment A

The premergence (soil) herbicidal activity of compounds of the invention was evaluated by planting seeds of barnyardgrass, garden cress, downy brome, velvetleaf, yellow foxtail, and sicklepod in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyard grass and garden cress seeds contained one milligram of the test compound per tube, and contained 0.1 milligram of test compound per each tube containing the seeds of the other plants. The dosages were approximately twenty and two pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
|---|---|
| 9 | No living tissue |
| 8 | Plant severely damaged and expected to die |
| 7 | Plant badly damaged, but expected to live |
| 6 | Moderate plant damage, but complete recovery expected |
| 5 | Intermediate damage (probably unacceptable damage for crop plants) |
| 3-4 | Observable damage |
| 1-2 | Plant slightly affected, possibly by the chemical, possibly due to biological variability |
| 0 | No visible effect |

The postemergence (foliar) herbicidal activity of Compounds of the Invention was evaluated by spraying 10-day-old large crabgrass plants, 13-day-old redroot pigweed plants, 6-day-old downy brome plants, 9-day-old velvetleaf plants, 9-day-old yellow foxtail plants and 9-day-old sicklepod plants to runoff with a liquid formulation of the test compound. The crabgrass and pigweed plants were sprayed with 2.4 milliliters of a 0.25% solution (about ten pounds of the test compound per acre), and other plants were sprayed with 2.4 milliliters of a 0.025% solution (about one pound of the test compound per acre). The sprayed plants were held under controlled conditions of temperature, moisture and light for 7 to 8 days and the effect of the test compound was then evaluated visually, the results being rated on the 0 to 9 scale described above.

Results of the preemergence and postemergence herbicidal activity tests conducted on the compounds of the invention are set forth in Table I below.

TABLE I

| | HERBICIDAL ACTIVITY | | | | | | | | | | | |
|---|---|---|---|---|---|---|---|---|---|---|---|---|
| | Preemergence | | | | | | Postemergence | | | | | |
| Embodiment | Barnyard-grass | Garden Cress | Downy Brome | Velvet-leaf | Yellow Foxtail | Sickle-pod | Crab-grass | Pig-weed | Johnson-grass | Velvet-leaf | Yellow Foxtail | Sickle-pod |
| V | 9 | 7 | 9 | 5 | 8 | 3 | 7 | 7 | 5 | 6 | 7 | 7 |
| VI | 9 | 6 | 8 | 5 | 8 | 4 | 7 | 6 | 2 | 5 | 2 | 7 |
| VII | 9 | 8 | 9 | 7 | 8 | 7 | 9 | 7 | 7 | 7 | 7 | 5 |
| XIX | 9 | 8 | 9 | 7 | 8 | 6 | 9 | 7 | 4 | 7 | 7 | 4 |
| XXI | 9 | 7 | 6 | 6 | 5 | 3 | 4 | 4 | 2 | 7 | 2 | 4 |
| XX | 9 | 7 | 9 | 7 | 9 | 4 | 8 | 6 | 0 | 7 | 5 | 3 |
| VIII | 9 | 7 | 9 | 7 | 9 | 4 | 8 | 5 | 3 | 7 | 7 | 5 |
| IX | 9 | 7 | 8 | 6 | 8 | 6 | 7 | 6 | 3 | 6 | 6 | 7 |
| XVI | 9 | 8 | 9 | 7 | 8 | 6 | 8 | 6 | 0 | 6 | 8 | 3 |
| XXXIII | 8 | 7 | 3 | 2 | 0 | 0 | 2 | 6 | 0 | 0 | 0 | 0 |
| XXVII | 9 | 7 | 8 | 6 | 8 | 4 | 7 | 6 | 6 | 5 | 8 | 4 |

We claim:
1. A compound of the formula I

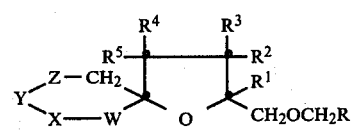

wherein $R^1$, $R^2$, $R^3$, $R^4$, $R^5$ each individually is a hydrogen atom or an alkyl group containing from 1 to 4 carbon atoms; W is an oxygen atom or —$CH_2$—; X is an oxygen atom or —$CH_{26}$—; Y is a carbon-carbon bond, an oxygen atom, —$CH_2$—, —$C_2H_4$— or —$CHR^6$— in which $R^6$ is an alkoxymethyl group containing from 1 to 4 carbon atoms in the alkyl portion thereof; Z is a carbon-carbon bond, an oxygen atom, —$CH_2$—, or —$C_2$-

$H_4$—; with the proviso that no two adjacent of W, X, Y and Z are simultaneously either oxygen atoms or —$C_2H_4$— and the sum of ring atoms in W, X, Y and Z is an integer of from 2 to 5; and R is an alkenyl or alkynyl group containing from 2 to 4 carbon atoms, a 2-furanyl group, a 2-pyridinyl group or a phenyl group optionally substituted by one or more of halogen, amino, monoalkylamino, dialkylamino, alkyl, haloalkyl, alkoxy, haloalkoxy or alkylthio.

2. A compound according to claim 1 wherein $R^1$ is a hydrogen atom, a methyl group or an ethyl group.

3. A compound according to claim 1 wherein $R^2$, $R^3$, $R^4$ and $R^5$ each is a hydrogen atom.

4. A compound according to claim 1 wherein Y is an oxygen atom, —$CHR^6$—, —$CH_2$— or —$C_2H_4$—; Z is an oxygen atom or —$CH_2$— and the sum of the ring atoms in W, X, Y, and Z is an integer of from 3 to 5.

5. A compound according to claim 1 wherein R is an ethynyl group, a 2-pyridinyl group or a phenyl group optionally substituted by 1 or 2 chlorine or fluorine atoms or methyl groups.

6. A compound according to claim 5 wherein $R^1$ is a hydrogen atom, a methyl group or an ethyl group; $R^2$, $R^3$, $R^4$ and $R^5$ each is a hydrogen atom; Y is an oxygen atom, —$CHR^6$—, —$CH_2$— or —$C_2H_4$—; Z is an oxygen atom or —$CH_2$— and the sum of the ring atoms in W, X, Y and Z is an integer of from 3 to 5.

7. A compound according to claim 6 wherein $R^1$ is an ethyl group.

8. A compound according to claim 7 wherein R is a phenyl, a 2-fluorophenyl, a 2-methylphenyl, a 2-chlorophenyl or a 2-pyridinyl group.

9. A compound according to claim 8 wherein W and Z each is —$CH_2$—; and one of X and Y is —$CH_2$—; and the other is an oxygen atom.

10. A compound according to claim 8 wherein W is —$CH_2$—; X and Z each is an oxygen atom; and Y is —$C_2H_4$—.

11. A compound according to claims 8, 9 or 10 wherein R is a 2-fluorophenyl group.

12. A compound of the formula II

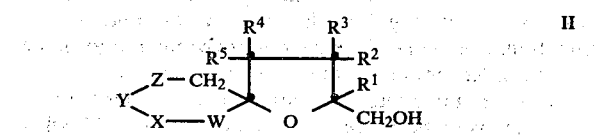

wherein $R^1$, $R^2$, $R^3$, $R^4$ and $R^5$ each individually is a hydrogen atom or an alkyl group containing from 1 to 4 carbon atoms; W is an oxygen atom or —$CH_2$—; X is an oxygen atom or —$CH_2$—; Y is a carbon-carbon bond, an oxygen atom, —$CH_2$—, —$C_2H_4$— or $CHR^6$ in which $R^6$ is an alkoxymethyl group containing 1 to 4 carbon atoms in the alkyl portion thereof; Z is a carbon-carbon bond, an oxygen atom, —$CH_2$— or —$C_2H_4$—; with the proviso that no two adjacent of W, X, Y and Z are simultaneously either oxygen atoms or —$C_2H_4$— and the sum of ring atoms in W, X, Y and Z is an integer of from 2 to 5.

13. A composition for controlling undesirable plant growth consisting essentially of a herbicidally effective amount of a compound according to claim 1 and at least one surface-active agent or carrier.

14. A method of controlling undesirable plant growth at a locus consisting essentially of applying to the locus or the plants a herbicidally effective amount of a compound according to claim 1.

* * * * *